(12) United States Patent
Kim et al.

(10) Patent No.: US 10,519,490 B2
(45) Date of Patent: Dec. 31, 2019

(54) POROUS MATRIX COMPRISING NUCLEIC ACID PRIMER-CARBON MATERIAL COMPOSITES AND PCR USING THE SAME

(71) Applicant: Korea Institute of Science and Technology, Seoul (KR)

(72) Inventors: Sang Kyung Kim, Seoul (KR); Seungwon Jung, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 261 days.

(21) Appl. No.: 15/499,005

(22) Filed: Apr. 27, 2017

(65) Prior Publication Data

US 2017/0321265 A1    Nov. 9, 2017

(30) Foreign Application Priority Data

May 3, 2016   (KR) ........................ 10-2016-0054875

(51) Int. Cl.
   *C12Q 1/68*      (2018.01)
   *C12Q 1/6853*    (2018.01)
   *C12Q 1/686*     (2018.01)

(52) U.S. Cl.
   CPC ........... *C12Q 1/6853* (2013.01); *C12Q 1/686* (2013.01)

(58) Field of Classification Search
   CPC ................ C12Q 1/6834; C12Q 1/6853; C12Q 2563/157; B01J 2219/00644
   See application file for complete search history.

(56) References Cited

U.S. PATENT DOCUMENTS

| | | | |
|---|---|---|---|
| 7,498,423 B2 | 3/2009 | Zheng et al. | |
| 7,955,802 B2 | 6/2011 | Whitman et al. | |
| 2006/0019264 A1 | 1/2006 | Attiya et al. | |
| 2009/0155891 A1 | 6/2009 | Tamaoki et al. | |
| 2009/0203083 A1 | 8/2009 | Mauritz | |
| 2015/0080251 A1 | 3/2015 | Min et al. | |
| 2016/0265028 A1 | 9/2016 | Kim et al. | |

FOREIGN PATENT DOCUMENTS

| | | |
|---|---|---|
| KR | 10-0791699 B1 | 10/2008 |
| KR | 10-2008-0103548 A | 11/2008 |
| KR | 10-2015-0048964 A | 5/2015 |
| WO | WO 2004/048255 A2 | 6/2004 |
| WO | WO 2011/068518 A1 | 6/2011 |
| WO | WO 2015/065005 A1 | 5/2015 |
| WO | WO 2016/065115 A1 | 4/2016 |

OTHER PUBLICATIONS

Lu, Jiong et al., "Transforming c60 Molecules into Graphene Quantum Dots", *Nature Nanotechnology*, vol. 6, 2011 (pp. 247-252).
Zhao, Bin et al., "Carbon Nanotubes Multifunctionalized by Rolling Circle Amplification and Their Application for Highly Sensitive Detection of Cancer Markers", *Small*, vol. 9, 2013 (pp. 2595-2601).
Zhu, Meidong et al., "Interactions of the primers and Mg2+ with graphene quantum dots enhance PCR performance", *RSC Advances*, vol. 5, 2015 (pp. 74515-74522).
European Search Report dated Sep. 25, 2017 in corresponding European Patent Application No. 17163716.8 (22 pages in English).
Kim, Hyo Ryoung, et al., "Facilitation of Polymerase Chain Reaction with Poly(ethylene glycol)-Engrafted Graphene Oxide Analogous to a Single-Stranded-DNA Binding Protein", *Applied Materials & Interfaces*, 2016, pp. 33521-33528 (8 pages in English).
Jung, Seungwon, et al., "Extensible Multiplex Real-time PCR of MicroRNA Using Microparticles", *Scientific Reports*, 2016, pp. 1-7 (7 pages in English).
European Office Action dated May 20, 2019 in corresponding European Patent Application No. 17 163 716.8-1118.

*Primary Examiner* — David C Thomas
(74) *Attorney, Agent, or Firm* — NSIP Law

(57) ABSTRACT

A porous matrix according to the present disclosure, wherein a nucleic acid primer-carbon material composite in which one or more nucleic acid primer of a forward primer and a reverse primer as a polymerase chain reaction (PCR) primer is bound to a carbon material is included in the pores of the matrix, provides improved amplification efficiency as compared to a matrix wherein the nucleic acid primer is present on the outer surface of the matrix or a porous matrix wherein the nucleic acid primer is directly fixed inside pores. The porous matrix of the present disclosure can effectively detect various kinds of target nucleic acids simultaneously and analyze them in real time by varying the kinds of the nucleic acid primers included in the matrix. Therefore, it is useful in amplifying multiple nucleic acids.

21 Claims, 5 Drawing Sheets
Specification includes a Sequence Listing.

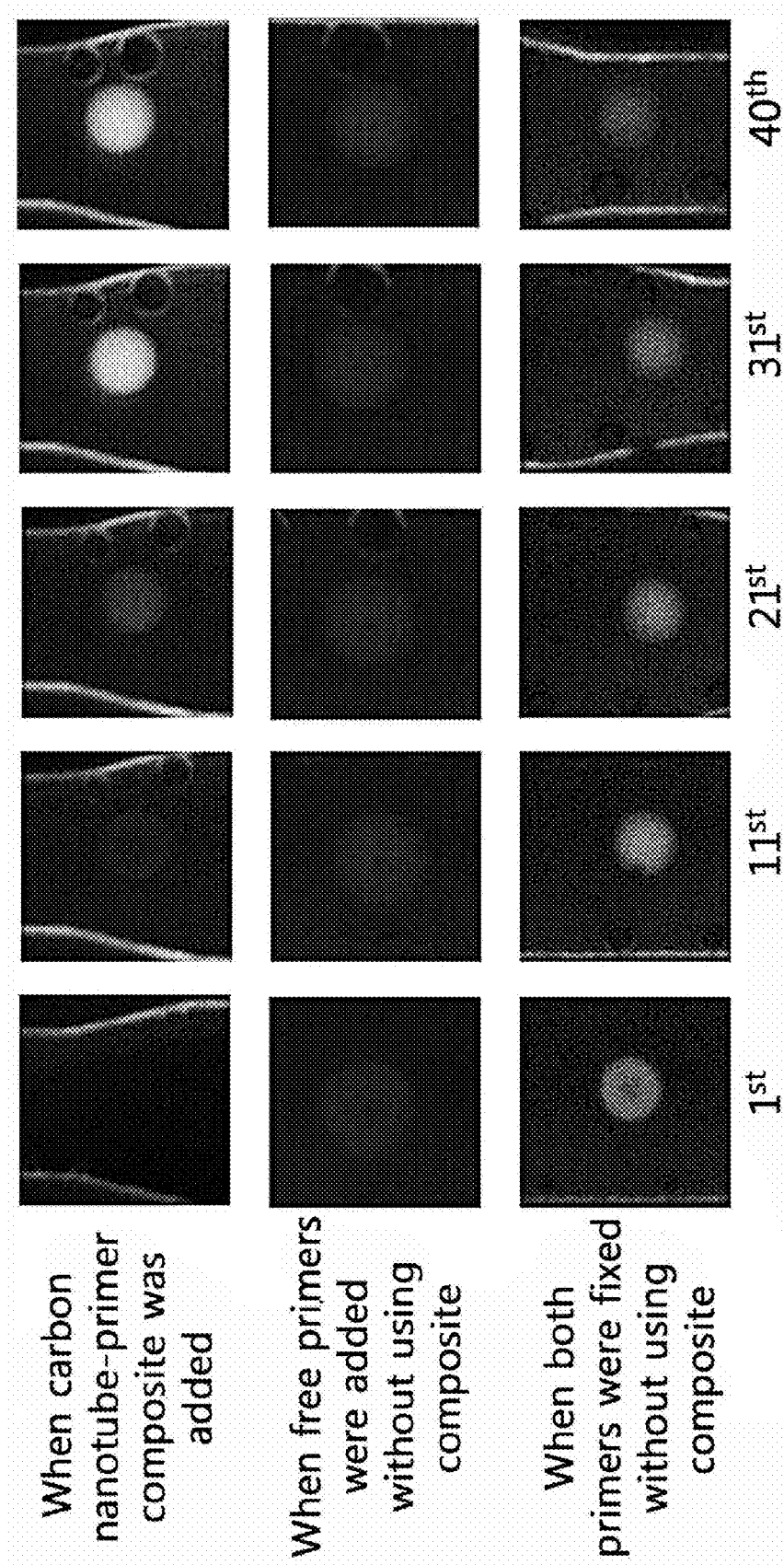

POROUS MATRIX COMPRISING NUCLEIC ACID PRIMER-CARBON MATERIAL COMPOSITES AND PCR USING THE SAME

DESCRIPTION OF GOVERNMENT-SUPPORTED RESEARCH AND DEVELOPMENT

This research was organized by the Korea Institute of Science and Technology with support from the medium-standing researchers support project of the Ministry of Science, ICT and Future Planning (sponsored by: National Research Foundation of Korea, project name: Development of technology for solid-liquid hybrid array nucleic acid analysis for diagnosis of multiple genetic markers, project number: 1711032052).

CROSS-REFERENCE TO RELATED APPLICATIONS

This application claims priority under 35 U.S.C. § 119(e), 120 and 365(c) to Korean Patent Application No. 10-2016-0054875, filed on May 3, 2016, the entire disclosures of each of which are incorporated herein by reference for all purposes.

BACKGROUND

1. Field

The present disclosure relates to a porous matrix containing a nucleic acid primer and a method for amplifying a nucleic acid using the same.

2. Description of Related Art

PCR techniques include end-point PCR, real-time PCR, digital PCR, etc. In particular, the method for amplifying multiple nucleic acids in real time (multiplex real-time PCR) is widely used in diagnosis of diseases because various biomarkers can be detected through one experiment in one chamber and quantitative analysis is possible in real time.

However, with the method of utilizing the color of a probe and the melting point of a primer, which is the most commonly used method in amplification of multiple nucleic acids, accurate detection is difficult when there are many targets to be detected due to interference between them. Accordingly, it is difficult to be used when accurate diagnosis of a disease is necessary through quick analysis of various kinds of different nucleic acids such as in point-of-care technology (POCT).

REFERENCES OF THE RELATED ART

Patent Documents

Korean Patent Registration No. 10-0794699.
Korean Patent Publication No. 10-2008-0103548.

SUMMARY

The present disclosure is directed to providing a porous matrix containing both a forward primer and a reverse primer of a nucleic acid and having superior amplification efficiency and a method for amplifying a nucleic acid, which is capable of accurately analyzing various kinds of nucleic acids simultaneously in real time using the matrix.

In an aspect, the present disclosure provides, as a novel means for providing a nucleic acid primer fixed inside a matrix, a porous matrix for an apparatus for amplifying a nucleic acid, which contains a nucleic acid primer-carbon material composite wherein one or more nucleic acid primer of a forward primer and a reverse primer is bound to a carbon material inside the pores of the matrix.

In another aspect, the present disclosure provides an apparatus for amplifying a nucleic acid, which includes the porous matrix and an array whose surface is patterned such that the porous matrix is arranged in the form of a well.

In another aspect, the present disclosure provides a method for amplifying a nucleic acid, which includes arranging the one or more porous matrix on an array whose surface is patterned in the form of a well by injecting the porous matrix into a chamber containing the array, introducing a solution containing one or more target nucleic acid into the pores of the porous matrix by injecting the solution into a chamber of an apparatus for amplifying a nucleic acid, and amplifying the target nucleic acid through polymerase chain reaction (PCR).

The porous matrix according to the present disclosure, wherein a nucleic acid primer-carbon material composite in which one or more nucleic acid primer of a forward primer and a reverse primer as a polymerase chain reaction (PCR) primer is bound to a carbon material is included in the pores of the matrix, provides improved amplification efficiency as compared to a matrix wherein the nucleic acid primer is present on the outer surface of the matrix or a porous matrix wherein the nucleic acid primer is directly fixed inside pores.

The nucleic acid primer-carbon material composite improves reactivity with a target nucleic acid because the carbon material is fixed inside the porous matrix, and, thus, the nucleic acid primer is separated from the carbon material and can move freely during amplification of the nucleic acid.

Accordingly, the porous matrix of the present disclosure can effectively detect various kinds of target nucleic acids simultaneously and analyze them in real time by varying the kinds of the nucleic acid primers included in the matrix. Therefore, it can be used for amplification of multiple nucleic acids in real time and is useful in accurately diagnosing diseases by quickly analyzing various kinds of different nucleic acids simultaneously.

BRIEF DESCRIPTION OF THE DRAWINGS

In FIG. 1, the short and thick lines denote carbon nanotubes, the long lines denote PEG polymers, the black dots denote chemical crosslinking sites and the white void space denotes pores.

FIG. 5 compares the PCR efficiency of a porous matrix according to an exemplary embodiment of the present disclosure (carbon nanotube-primer composite) with the cases where forward and reverse primers are fixed without a composite and where the both primers are not fixed (free primers) without a composite.

DETAILED DESCRIPTION

Hereinafter, the present disclosure is described in detail.

Figure 1:
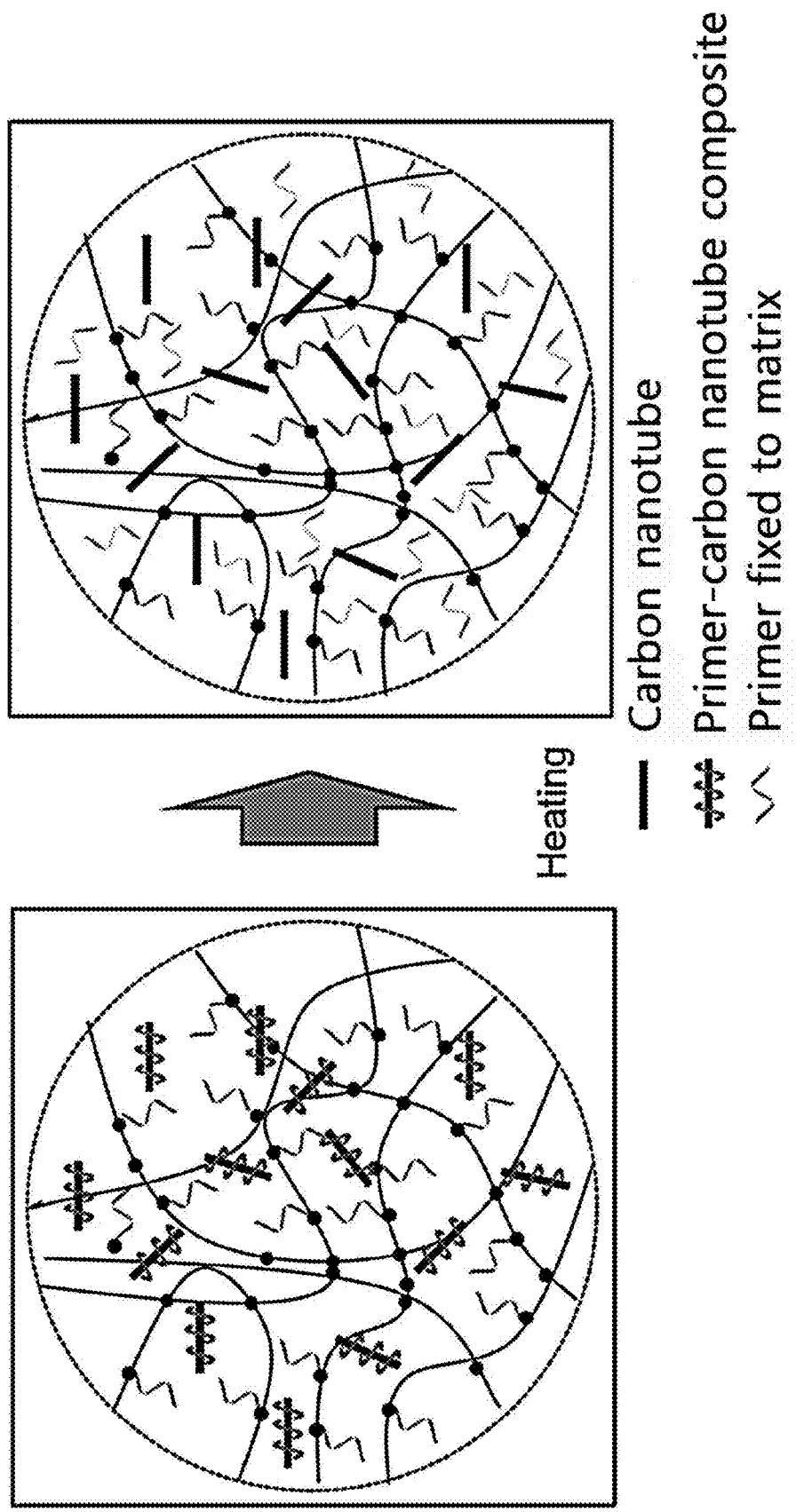
FIG. 1 schematically shows a porous matrix (left) containing a nucleic acid primer-carbon material composite and separation of a nucleic acid primer from the composite during nucleic acid amplification with increase in temperature (right).

An exemplary embodiment of the present disclosure provides a porous matrix for an apparatus for amplifying a nucleic acid, which contains a nucleic acid primer-carbon material composite wherein one or more nucleic acid primer of a forward primer and a reverse primer is bound to a carbon material inside the pores of the matrix In an exemplary embodiment, the nucleic acid primer-carbon material composite is formed from pi-pi stacking of a part of the hexagonal structure of carbon in the carbon material and a part of the hexagonal structure of a base of the nucleic acid primer. Specifically, the carbon material and the nucleic acid primer form the nucleic acid primer-carbon material composite as the hexagonal structure formed by the carbon atoms on the wall of the carbon material non-covalently reacts with the hexagonal structure formed by the base in the nucleic acid primer through pi-pi stacking. In the nucleic acid primer-carbon material composite, the nucleic acid primer can be stably present in the porous matrix without being separated from the carbon material before PCR during washing of the porous matrix or despite other change in environments due to superior binding between the nucleic acid primer and the carbon material in the composite. In an exemplary embodiment, the nucleic acid primer may be separated from the carbon material during amplification of a nucleic acid and react with a target nucleic acid. For example, the nucleic acid primer may be separated from the carbon material during amplification of the nucleic acid when the temperature is raised to about 50° C. or higher (see FIG. 1). When the nucleic acid amplification is conducted under an isothermal condition (isothermal PCR), the nucleic acid primer may be separated from the carbon material when it meets a complementary template.

In an exemplary embodiment of the present disclosure, the nucleic acid primer-carbon material composite may be uniformly distributed inside the porous matrix due to repulsion by the negative charge of the nucleic acid backbone of the nucleic acid primer.

In an exemplary embodiment, the carbon material of the nucleic acid primer-carbon material composite may be any substance containing hexagonally arranged carbon atoms without limitation. For example, one or more of graphite, graphene, graphene oxide, highly oriented pyrolytic graphite (HOPG), carbon nanotube and fullerene may be used. And, the nucleic acid primer may be, for example, one or more nucleic acid of DNA, RNA, LNA and PNA, although not being limited thereto. The nucleic acid primer may be 10-100 base pairs (bp), more specifically 20-50 base pairs. However, the particular sequence and length of the nucleic acid primer may be varied depending on the target nucleic acid without limitation. In an exemplary embodiment, the nucleic acid primer-carbon material composite may be formed as one or more carbon material and one or more nucleic acid primer are bound in one composite. For example, the composite may be formed as one or more carbon material is bound to two or more nucleic acid primers with different base sequences. Also, the composite may be formed as two or more carbon materials are bound to one or more nucleic acid primer.

In an exemplary embodiment, the nucleic acid primer-carbon material composite may further contain a third probe in addition to the nucleic acid primer to further increase selectivity. For example, the third probe may be a TaqMan™ probe.

In an exemplary embodiment, the porous matrix may contain the nucleic acid primer-carbon material composite at a concentration of 1 µM to 1 mM based on the primer bound to the composite. In an exemplary embodiment, the porous matrix may contain 0.1-10 µg of the carbon material and 10 amol to 10 pmol of the nucleic acid primer.

In an exemplary embodiment, the porous matrix may be one wherein the carbon material of the nucleic acid primer-carbon material composite is fixed inside the pores of the porous matrix. The nucleic acid primer-carbon material composite may be one wherein the carbon material is fixed inside the pores of the porous matrix physically and/or chemically. In an exemplary embodiment, carbon nanotube, which has a small diameter but a long length, as the carbon material of the nucleic acid primer-carbon material composite may be physically fixed inside the pores of the porous matrix which are larger in size than the diameter. In an exemplary embodiment, the carbon material of the nucleic acid primer-carbon material composite may be chemically fixed inside the pores of the porous matrix using a functional group such as an amine group, a carboxyl group, an acryl group, etc.

As the carbon material is fixed inside the pores of the porous matrix, the nucleic acid primer of the composite can be separated from the composite and move freely inside the pores of the porous matrix during PCR. Accordingly, the porous matrix according to an exemplary embodiment of the present disclosure can provide superior amplification efficiency because both the forward primer and the reverse primer are fixed inside the pores of the matrix but it exhibits improved reactivity and selectivity as compared to the existing matrix wherein the two primers are fixed inside particles.

In an exemplary embodiment of the present disclosure, one of the forward and reverse primers included in the porous matrix may form the nucleic acid primer-carbon material composite, such that the carbon material is fixed inside the pores of the matrix, and the other nucleic acid primer may be fixed inside the pores of the matrix without forming the nucleic acid primer-carbon material composite. The nucleic acid primer which is fixed inside the pores of the matrix without forming the nucleic acid primer-carbon material composite may be fixed through cross-linking with the matrix. In an exemplary embodiment, the nucleic acid primer may be, for example, one or more nucleic acid of DNA, RNA, LNA and PNA, although not being limited thereto. The nucleic acid primer may be 10-100 base pairs (bp), more specifically 20-50 base pairs. However, the particular sequence and length of the nucleic acid primer may be varied depending on the target nucleic acid without limitation.

For example, the porous matrix according to an exemplary embodiment of the present disclosure may have an average particle diameter of 10 µm to 5 mm, more specifically 100-600 µm. The shape of the porous matrix is not limited as long as it is a 3-dimensional matrix that can have pores inside thereof. For example, it may have a spherical, semispherical or disc shape. The porous matrix may be prepared from any solidifiable polymer (pre-polymer) without limitation. Specifically, a hydrophilic polymer such as polyethylene glycol diacrylate (PEG-DA) or polyacrylamide (PAM) may be used. Also, in an exemplary embodiment, the porosity of the porous matrix is 10-95 vol %, more specifically 60-80 vol %, based on the total volume of the porous matrix. Outside this range, the porosity or stability of the matrix may decrease.

Also, in an exemplary embodiment of the present disclosure, the porous matrix may further contain one or more of an encoder providing information of the nucleic acid primer and a fluorescent probe providing quantitative information of the amplified nucleic acid. The encoder refers to a substance which distinguishes the nucleic acid primer in the porous matrix based on color, shape, etc. For example, dyes exhibiting fluorescence of various colors, quantum dots or metals, plastics, glass, silicon, etc. of particular shape may be used. Otherwise, without using the encoder, the nucleic acid primer in the porous matrix may be distinguished by changing the size or shape of the porous matrix itself or specifically marking the surface of the porous matrix. Alternatively, the nucleic acid primer in the porous matrix may be distinguished by specifying the position in the array of the porous matrix.

In an exemplary embodiment of the present disclosure, a method for preparing the porous matrix may include: a step of preparing a primer-carbon material composite solution by adding a carbon material to a solution containing one or more primer of a forward primer and a reverse primer and binding the primer with the carbon material; a step of preparing a pre-polymer solution by mixing the primer-carbon material composite solution with a pre-polymer, a photoinitiator and a pore inducing polymer (porogen); a step of preparing a matrix by microspotting the pre-polymer solution into a droplet form and curing the same; and a step of forming pores inside the matrix by removing the pore inducing polymer from the matrix.

The "pre-polymer" refers to a preliminary polymer whose polymerization or polycondensation has been stopped at an appropriate stage for easy molding of a polymer. In the present disclosure, it refers to a polymer in an easily moldable state before it is solidified.

In an exemplary embodiment, in the step of preparing the primer-carbon material composite solution, the primer-carbon material composite solution may be prepared using a solution containing one of the forward and reverse primers. And, the pre-polymer solution may further contain the other primer of the forward and reverse primers not contained in the primer-carbon material composite solution and the primer may be fixed inside the matrix without forming the primer-carbon material composite.

The step of microspotting the pre-polymer solution into a droplet form may be performed by using a microchannel, a piezoelectric device, a solenoid valve, a microspotter, etc. Through this, matrices of various shapes and sizes can be prepared.

To take a method of using a microchannel as an example, after preparing a cross-shaped microchannel, an oil may be passed continuously through one channel and the pre-polymer solution may be passed discontinuously through the other channel, so that the matrix forming solution is dispersed in the oil at the crossing of the channels. The shape and size of the droplet particles passing through the channel may be controlled by controlling the flow rate of the oil and the pre-polymer solution and their ratio.

By injecting different nucleic acid primers depending on the target nucleic acids, a plurality of porous matrices containing different nucleic acid primers can be prepared. The pre-polymer solution may further contain one or more of an encoder providing information of the nucleic acid primer and a fluorescent probe providing quantitative information of the amplified nucleic acid.

In an exemplary embodiment, the step of preparing the pre-polymer solution may further include controlling the size of the pores formed in the porous matrix by changing the size of the pore inducing polymer contained in the solution. For example, the pore inducing polymer may be polyethylene glycol (PEG) or polyacrylamide (PAM). Specifically, PEG 200, PEG 300, PEG 400, PEG 600, PEG 1000, PEG 1500, PEG 2000, PEG 3000, PEG 3350, PEG 4000, PEG 6000, PEG 8000, PEG 10000, PEG 12000, PEG 20000, PEG 35000, PEG 40000, etc. (available from Sigma Aldrich) may be used as the polyethylene glycol.

In an exemplary embodiment of the present disclosure, the porous matrix is cured while maintaining the shape of the porous matrix before the curing. The curing method is not limited as long as the shape can be maintained. For example, optical, chemical or thermal curing may be used.

In another exemplary embodiment, the present disclosure provides an apparatus for amplifying a nucleic acid, which includes: the one or more porous matrix; and an array whose surface is patterned such that the porous matrix is arranged in the form of a well.

In an exemplary embodiment, the array whose surface is patterned in the form of a well may be prepared from glass, plastics, polymers, silicon, etc. without limitation. In an exemplary embodiment, the apparatus for amplifying a nucleic acid may include a plurality of porous matrices containing nucleic acid primers for different target nucleic acids or nucleic acid primers and encoders in different wells for detection of various kinds of target nucleic acids simultaneously in one channel. In an exemplary embodiment, the array may fix the porous matrix to the bottom of the well. The fixing may be achieved by making the bottom have a surface having an acrylate group.

In another exemplary embodiment, the present disclosure provides a method for amplifying a nucleic acid, which includes: a step of arranging the one or porous matrix on an array whose surface is patterned in the form of a well by injecting the porous matrix into a chamber containing the array; a step of introducing a solution containing one or more target nucleic acid into the pores of the porous matrix by injecting the solution into a chamber of an apparatus for amplifying a nucleic acid; and a step of amplifying the target nucleic acid through polymerase chain reaction (PCR). In an exemplary embodiment, the one or more porous matrix may contain different primers.

In an exemplary embodiment, in step of amplifying the target nucleic acid, the target nucleic acid may be amplified as the nucleic acid primer of the nucleic acid primer-carbon material composite is separated from the carbon material. In an exemplary embodiment, the method for amplifying a nucleic acid may further include, simultaneously with the step of amplifying the target nucleic acid, a step of quantitatively analyzing the nucleic acid polymerized in the one or more porous matrix in real time. Through this, different target nucleic acids may be detected and quantitatively analyzed in real time while they are amplified.

Hereinafter, the present disclosure is described in detail through examples. However, the following examples are for illustrative purposes only and it will be apparent to those of ordinary skill in the art that the scope of the present disclosure is not limited by the examples.

[Example] Preparation of Porous Matrix

A porous matrix according to an exemplary embodiment of the present disclosure was prepared as follows.

First, a primer-carbon nanotube composite solution was prepared by adding 0.1 µg of carbon nanotube to a 1 mM solution of a forward primer for detecting *Salmonella* (Integrated DNA Technologies) and dispersing through sonication and centrifugation. Then, a pre-polymer solution was prepared by mixing PEG 700DA (pre-polymer, Sigma Aldrich), PEG 600 (pore inducing polymer, Sigma Aldrich), Darocur (Sigma Aldrich) as a photoinitiator and the forward primer-carbon nanotube composite solution at a volume ratio of 20:40:5:35 (20 µL:40 µL:5 µL:35 µL). The pre-polymer solution was mixed with a solution of a reverse primer having an acrylate group (Integrated DNA Technologies) at 9:1.

The base sequences of the forward primer and the reverse primer were as follows.

Forward primer: 5'-aattatcgcc acgttcgggc aattcgtta-3' (SEQ ID NO 1).

Reverse primer: 5'-tcaataatac cggccttcaa atcggcatc-3' (SEQ ID NO 2).

Then, the solution was microspotted into 25 nL droplets using a solenoid valve microspotter and then cured by irradiating UV. A porous matrix was prepared by washing the cured particles with purified water (D.I. water) and removing the pore inducing polymer (porogen) and the nucleic acid primer not fixed inside the porous matrix.

[Test Example 1] Amplification of Nucleic Acid Using Porous Matrix 1

A target nucleic acid was amplified using the porous matrix according to an exemplary embodiment of the present disclosure.

First, the porous matrix prepared in Example was injected into a channel of a PCR machine. Then, polymerase chain reaction (PCR) was conducted after injecting a PCR solution containing 8 µL of a PCR mastermix (Taq polymerase, dNTP SYBR Green I, Nanobiosys), 7 µL of distilled water (D.I. water) and 1 µL of a *Salmonella* DNA template ($1\times10^6$ copies of plasmid DNA) as a target nucleic acid into the chamber.

The PCR was conducted according to the following temperature cycles. A total of 40 cycles were conducted and quantitative analysis was made after every cycle by measuring the fluorescence intensity from the fluorescent probe of the amplified nucleic acid for 5 seconds.

Pre-denaturation: 95° C., 8 sec.
Denaturation: 95° C., 3 sec.
Annealing and extension: 72° C., 6 sec.

Figure 2:
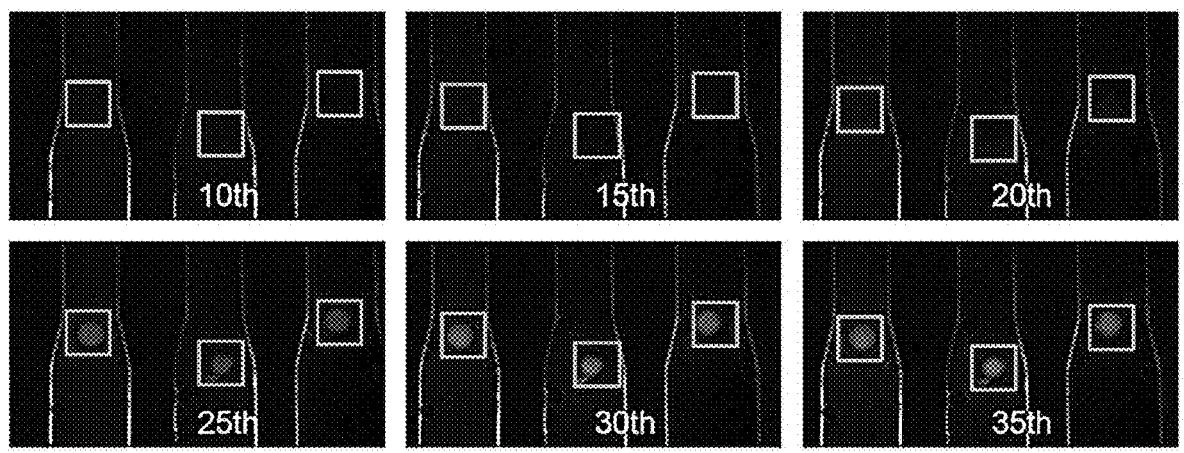
FIG. 2 shows a process of PCR using a porous matrix containing a nucleic acid primer-carbon material composite.
Figure 3:
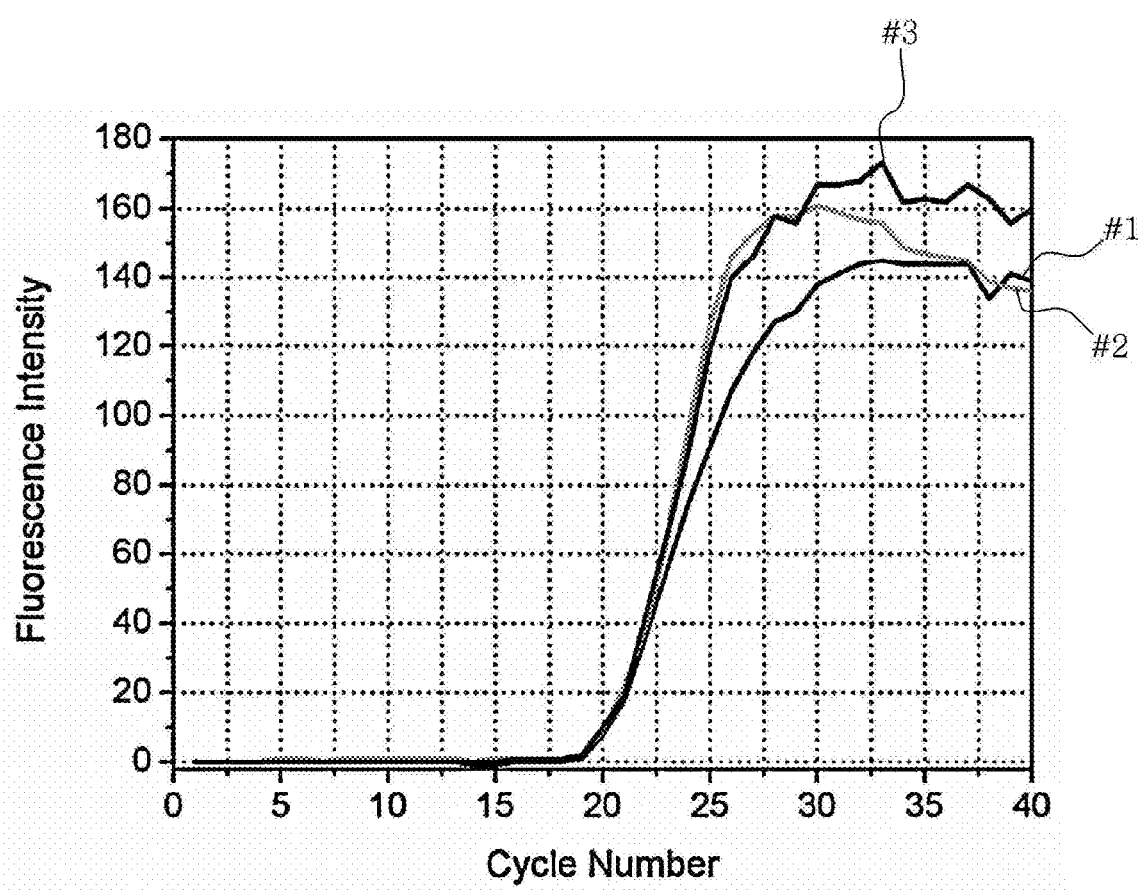
FIG. 3 shows a result of analyzing the PCR signal uniformity of nucleic acid primer-carbon material composites in three porous matrices (#1, #2, #3).

FIG. 2 and FIG. 3 show a result of investigating the uniformity and reproducibility of the porous matrix particle. Specifically, after adding the porous matrix prepared as described in Example to three different channels (#1, #2, #3) and then adding $1\times10^6$ copies of the *Salmonella* DNA template, PCR signal was compared. As seen from FIG. 2, the fluorescence intensity increased with cycle number. From FIG. 3, it can be seen that the signals were observed at the same positions. It was also confirmed that the fluorescence did not leak out of the particle due to sufficient washing.

Figure 4:
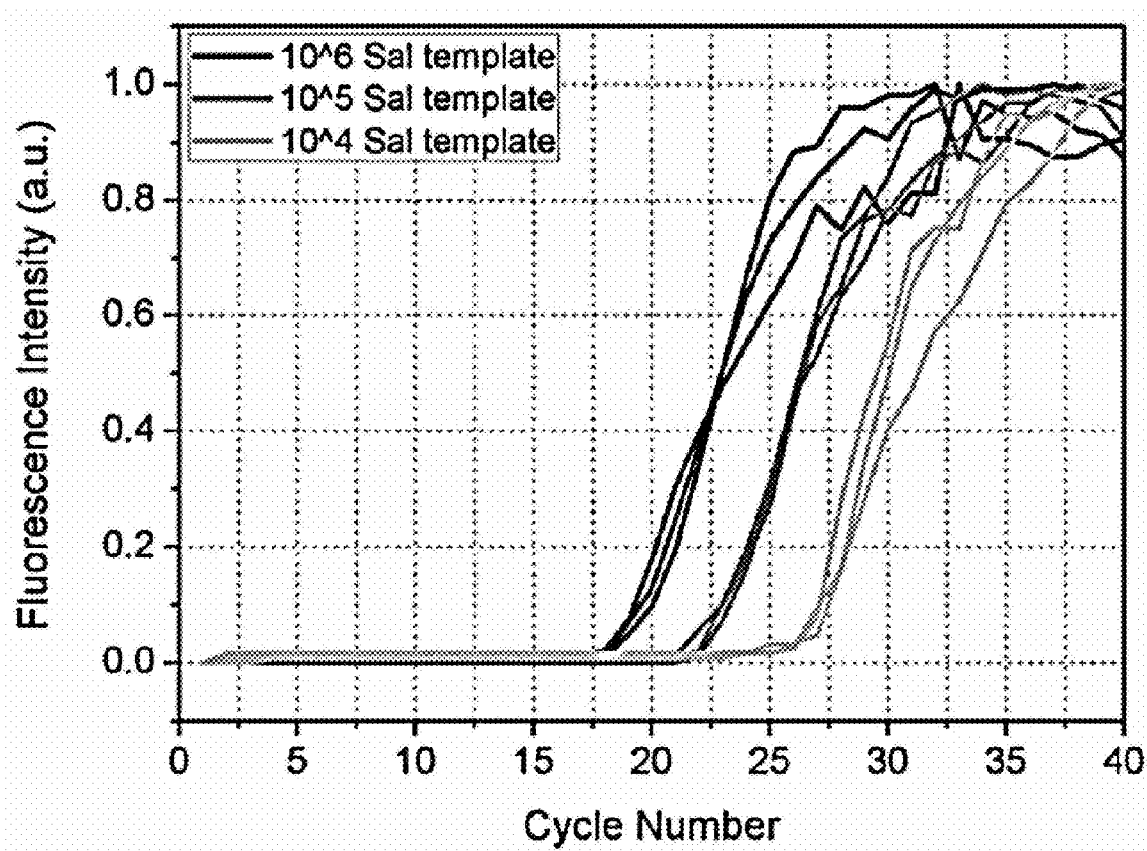
FIG. 4 shows a PCR analysis result depending on the concentration of a target nucleic acid.

FIG. 4 shows a result of conducting the same experiment while injecting the $1\times10^6$, $1\times10^5$ and $1\times10^4$ copies of the *Salmonella* DNA template per 1 µL. It can be seen that the PCR signals move leftward as the copy number decreases. As the concentration decreased 10-fold, the spacing between the curves was almost 3.3 which is an ideal gap for a 10-fold concentration difference.

[Test Example 2] Amplification of Nucleic Acid Using Porous Matrix 2

In order to investigate the PCR efficiency of the porous matrix according to an exemplary embodiment of the present disclosure, porous matrices containing forward and reverse primers without a primer-carbon material composite were prepared (Comparative Examples). Specifically, a porous matrix wherein both the forward and reverse primers were fixed and a porous matrix wherein both the forward and reverse primers were not fixed were prepared in the same manner as in the preparation of the porous matrix in Example, except that the primer-carbon nanotube composite solution was not prepared.

Then, polymerase chain reaction (PCR) was conducted in the same manner as in Test Example 1.

Quantitative analysis was made after every cycle by measuring the fluorescence intensity from the fluorescent probe of the amplified nucleic acid for 5 seconds. As seen from FIG. 5, fluorescence was observed only for the porous matrix containing the primer-carbon material composite according to the present disclosure (Example). Fluorescence was not observed for the porous matrices wherein the two primers were fixed or not fixed without using the composite (Comparative Examples). Of the two comparative examples, one in which the two primers were fixed without using the carbon material composite showed bright fluorescence in early cycles due to the high primer concentration but the fluorescence decreased gradually as PCR proceeded. This means that PCR does not occur or PCR efficiency is not good for the two comparative examples.

What is claimed is:

1. A porous matrix for an apparatus for amplifying a nucleic acid, which comprises a nucleic acid primer-carbon material composite wherein one or more nucleic acid primer of a forward primer and a reverse primer is bound to a carbon material inside the pores of the matrix,
 wherein the nucleic acid primer-carbon material composite is configured to release the nucleic acid primer for free movement inside the pores of the matrix in response to an amplification condition.

2. The porous matrix for an apparatus for amplifying a nucleic acid according to claim 1, wherein the carbon material of the nucleic acid primer-carbon material composite is uniformly distributed and fixed inside the pores of the matrix.

3. The porous matrix for an apparatus for amplifying a nucleic acid according to claim 1, wherein the nucleic acid primer-carbon material composite is formed from pi-pi stacking of a part of the hexagonal structure of carbon in the carbon material and a part of the hexagonal structure of a base of the nucleic acid primer.

4. The porous matrix for an apparatus for amplifying a nucleic acid according to claim 1, wherein the nucleic acid primer is detached from the carbon material in the nucleic acid primer-carbon material composite during amplification of a nucleic acid.

5. The porous matrix for an apparatus for amplifying a nucleic acid according to claim 1, wherein one of the forward and reverse primers forms the nucleic acid primer-carbon material composite, such that the carbon material is fixed inside the pores of the matrix, and the other nucleic acid primer is fixed inside the pores of the matrix without forming the nucleic acid primer-carbon material composite.

6. The porous matrix for an apparatus for amplifying a nucleic acid according to claim 5, wherein the nucleic acid primer which is fixed inside the pores of the matrix without forming the nucleic acid primer-carbon material composite is fixed through cross-linking with the matrix.

7. The porous matrix for an apparatus for amplifying a nucleic acid according to claim 1, wherein the carbon material of the nucleic acid primer-carbon material composite comprises one or more of graphite, graphene, graphene oxide, highly oriented pyrolytic graphite (HOPG), carbon nanotube and fullerene.

8. The porous matrix for an apparatus for amplifying a nucleic acid according to claim 1, wherein the nucleic acid primer of the nucleic acid primer-carbon material composite is one or more nucleic acid of DNA, RNA, LNA and PNA.

9. An apparatus for amplifying a nucleic acid, which comprises:
 one or more of the porous matrix according to claim 1; and
 an array whose surface is patterned such that the porous matrix is arranged in the form of a well.

10. The apparatus for amplifying a nucleic acid according to claim 9, wherein the apparatus for amplifying a nucleic acid comprises a plurality of porous matrices comprising nucleic acid primers for different target nucleic acids.

11. The apparatus for amplifying a nucleic acid according to claim 9, wherein the carbon material of the nucleic acid primer-carbon material composite is uniformly distributed and fixed inside the pores of the matrix.

12. The apparatus for amplifying a nucleic acid according to claim 9, wherein the nucleic acid primer is detached from the carbon material in the nucleic acid primer-carbon material composite during amplification of a nucleic acid.

13. The apparatus for amplifying a nucleic acid according to claim 9, wherein one of the forward and reverse primers forms the nucleic acid primer-carbon material composite, such that the carbon material is fixed inside the pores of the matrix, and the other nucleic acid primer is fixed inside the pores of the matrix without forming the nucleic acid primer-carbon material composite.

14. The apparatus for amplifying a nucleic acid according to claim 13, wherein the nucleic acid primer which is fixed inside the pores of the matrix without forming the nucleic acid primer-carbon material composite is fixed through cross-linking with the matrix.

15. A method for amplifying a nucleic acid, which comprises:
 arranging the one or more of the porous matrix according to claim 1 on an array whose surface is patterned in the form of a well by injecting the porous matrix into a chamber comprising the array;
 introducing a solution comprising one or more target nucleic acid into the pores of the porous matrix by injecting the solution into a chamber of an apparatus for amplifying a nucleic acid; and
 amplifying the target nucleic acid through polymerase chain reaction (PCR).

16. The method for amplifying a nucleic acid according to claim 15, wherein the one or more porous matrix comprises different nucleic acid primers.

17. The method for amplifying a nucleic acid according to claim 15, wherein, in the amplifying the target nucleic acid, the target nucleic acid is amplified as the nucleic acid primer of the nucleic acid primer-carbon material composite is separated from the carbon material.

18. The method for amplifying a nucleic acid according to claim 15, which further comprises, simultaneously with the amplifying the target nucleic acid, analyzing the nucleic acid polymerized in the one or more porous matrix in real time.

19. The method for amplifying a nucleic acid according to claim 15, wherein one of the forward and reverse primers forms the nucleic acid primer-carbon material composite, such that the carbon material is fixed inside the pores of the matrix, and the other nucleic acid primer is fixed inside the pores of the matrix without forming the nucleic acid primer-carbon material composite.

20. The method for amplifying a nucleic acid according to claim 19, wherein the nucleic acid primer which is fixed inside the pores of the matrix without forming the nucleic acid primer-carbon material composite is fixed through cross-linking with the matrix.

21. An apparatus for amplifying a nucleic acid, which comprises:
  a matrix having pores,
  a composite material comprising a nucleic acid primer bound to a carbon material fixed inside the pores of the matrix, wherein the nucleic acid primer is one of a forward primer and a reverse primer, and
  a nucleic acid primer, which is the other of the forward primer and the reverse primer, fixed inside the pores of the matrix and without forming a carbon material-bound composite.

* * * * *

SEQUENCE LISTING

<160> NUMBER OF SEQ ID NOS: 2

<210> SEQ ID NO 1
<211> LENGTH: 29
<212> TYPE: DNA
<213> ORGANISM: Artificial Sequence
<220> FEATURE:
<223> OTHER INFORMATION: Forward primer

<400> SEQUENCE: 1
aattatcgcc acgttcgggc aattcgtta                                       29

<210> SEQ ID NO 2

```
<211> LENGTH: 29
<212> TYPE: DNA
<213> ORGANISM: Artificial Sequence
<220> FEATURE:
<223> OTHER INFORMATION: Reverse primer

<400> SEQUENCE: 2
tcaataatac cggccttcaa atcggcatc                                           29
```